(12) United States Patent
Krupnik

(10) Patent No.: US 10,521,924 B2
(45) Date of Patent: *Dec. 31, 2019

(54) SYSTEM AND METHOD FOR SIZE ESTIMATION OF IN-VIVO OBJECTS

(71) Applicant: GIVEN IMAGING LTD., Yoqneam (IL)

(72) Inventor: Hagai Krupnik, Nofit (IL)

(73) Assignee: GIVEN IMAGING LTD., Yoqneam (IL)

( * ) Notice: Subject to any disclaimer, the term of this patent is extended or adjusted under 35 U.S.C. 154(b) by 134 days.

This patent is subject to a terminal disclaimer.

(21) Appl. No.: 15/821,770

(22) Filed: Nov. 23, 2017

(65) Prior Publication Data

US 2018/0096491 A1  Apr. 5, 2018

Related U.S. Application Data

(63) Continuation of application No. 14/918,000, filed as application No. PCT/IL2014/050865 on Oct. 1, 2014, now Pat. No. 9,911,203.

(Continued)

(51) Int. Cl.
*G06T 7/60* (2017.01)
*A61B 1/04* (2006.01)
(Continued)

(52) U.S. Cl.
CPC ............... *G06T 7/60* (2013.01); *A61B 1/041* (2013.01); *G06T 7/0012* (2013.01); *G06T 7/62* (2017.01);
(Continued)

(58) Field of Classification Search
CPC ............... G06T 7/0012; G06T 2200/04; G06T 2200/24; G06T 7/62; A61B 1/041
See application file for complete search history.

(56) References Cited

U.S. PATENT DOCUMENTS

| 5,604,531 A | 2/1997 | Iddan et al. |
| 7,009,634 B2 | 3/2006 | Iddan et al. |

(Continued)

FOREIGN PATENT DOCUMENTS

| EP | 2 557 447 | 2/2013 |
| WO | WO 2012/136669 | 10/2012 |
| WO | WO 2012/136669 A2 | 10/2012 |

OTHER PUBLICATIONS

Office Action for Korean Patent Application No. 201480050849.8, dated Sep. 18, 2018.

*Primary Examiner* — Utpal D Shah
(74) *Attorney, Agent, or Firm* — Pearl Cohen Zedek Latzer Baratz LLP

(57) ABSTRACT

A system, method and virtual tool for size estimation of in-vivo objects includes receiving and displaying a two-dimensional image of in-vivo objects obtained by in-vivo imaging device; receiving indication of a selected area representing a point of interest from the user via a user input device; estimating depth of a plurality of image pixels around the selected area; calculating three-dimensional coordinates representation of the plurality of image points, based on the estimated depths; casting a virtual tool of a known size onto the three-dimensional representation; and projecting the virtual tool onto the two-dimensional image to create a cursor having a two-dimensional shape on the displayed image.

20 Claims, 6 Drawing Sheets

Related U.S. Application Data

(60) Provisional application No. 61/885,573, filed on Oct. 2, 2013.

(51) Int. Cl.
*G06T 7/00* (2017.01)
*G06T 7/62* (2017.01)

(52) U.S. Cl.
CPC .............. *G06K 2209/05* (2013.01); *G06T 2207/10068* (2013.01); *G06T 2207/20101* (2013.01); *G06T 2207/30028* (2013.01); *G06T 2207/30092* (2013.01)

(56) References Cited

U.S. PATENT DOCUMENTS

| | | | | |
|---|---|---|---|---|
| 7,551,955 | B2* | 6/2009 | Adler | A61B 1/041 |
| | | | | 382/128 |
| 7,876,939 | B2* | 1/2011 | Yankelevitz | A61B 5/1075 |
| | | | | 382/128 |
| 8,663,092 | B2* | 3/2014 | Pascal | A61B 1/00009 |
| | | | | 600/103 |
| 9,014,441 | B2 | 4/2015 | Truyen et al. | |
| 9,412,054 | B1* | 8/2016 | Krupnik | A61B 1/00009 |
| 2007/0016018 | A1 | 1/2007 | Kinicki | |
| 2009/0253954 | A1* | 10/2009 | Katayama | A61B 1/041 |
| | | | | 600/103 |
| 2010/0054579 | A1 | 3/2010 | Okutomi et al. | |
| 2010/0215245 | A1* | 8/2010 | Olivan Bescos | G06T 3/0006 |
| | | | | 382/133 |
| 2010/0246923 | A1 | 9/2010 | Nathaniel et al. | |
| 2010/0254579 | A1 | 10/2010 | Lee et al. | |
| 2010/0260383 | A1* | 10/2010 | Truyen | A61B 5/1072 |
| | | | | 382/106 |
| 2010/0318099 | A1* | 12/2010 | Itkowitz | A61B 34/30 |
| | | | | 606/130 |
| 2012/0082360 | A1 | 4/2012 | Florent | |
| 2013/0031498 | A1 | 1/2013 | Bagaria et al. | |
| 2014/0029815 | A1* | 1/2014 | Kadir | A61B 6/463 |
| | | | | 382/128 |
| 2014/0340404 | A1* | 11/2014 | Wang | G06T 15/20 |
| | | | | 345/427 |
| 2015/0187063 | A1* | 7/2015 | Takahashi | A61B 1/00009 |
| | | | | 382/128 |
| 2015/0371422 | A1* | 12/2015 | Kokemohr | G06T 11/60 |
| | | | | 382/128 |
| 2016/0196643 | A1* | 7/2016 | Bendall | G06T 7/50 |
| | | | | 382/108 |

\* cited by examiner

SYSTEM AND METHOD FOR SIZE ESTIMATION OF IN-VIVO OBJECTS

RELATED APPLICATION DATA

This application is a continuation of prior U.S. patent application Ser. No. 14/918,000 entitled "SYSTEM AND METHOD FOR SIZE ESTIMATION OF IN-VIVO OBJECTS", which entered the national phase on Mar. 10, 2016, which is a national phase Application of PCT International Application No. PCT/IL2014/050865, International Filing Date Oct. 1, 2014, published Apr. 9, 2015 as International Publication Number WO 2015/049684, which claims priority from U.S. Provisional Application No. 61/885,573, filed Oct. 2, 2013, all of which are incorporated herein by reference in their entirety.

FIELD OF THE INVENTION

The present invention relates to the field of estimating a geometrical parameter of objects in an image. More specifically, the present invention relates to estimating or determining a size of objects in an image. In particular, the present invention relates to images obtained by an in-vivo device, and to a virtual tool for estimating size of in-vivo objects, regions or tissues.

BACKGROUND OF THE INVENTION

Known devices may be helpful in providing in-vivo sensing, for example, using imaging techniques, systems and/or methods. One of the uses for such devices may be in detecting and/or identifying objects or tissues that may indicate in-vivo pathologies. Autonomous in-vivo sensing devices, e.g., swallowable or ingestible capsules or other devices may move through a body lumen, sensing, monitoring or otherwise obtaining data as they move along body lumens. Such autonomous in-vivo sensing devices may include, for example, an imager for obtaining images of a body cavity or lumen, such as the gastrointestinal (GI) tract. Such autonomous in-vivo sensing devices may include an optical system, a light source, a controller and optionally a transmitter and an antenna. Some of these devices use a wireless connection to transmit image data.

Different methods for estimating the size of objects imaged in a body lumen exist. For example, an in-vivo device may emit a laser beam and may further acquire an image of a spot on a tissue created by such beam as well as surrounding tissues or region. A distance of the spot from the in-vivo device may be calculated, e.g., based on the location of the spot in an image. Various parameters, coefficients or other information related to a color or other optical aspects of nearby tissue (that may be assumed to be in the same and known distance of the laser beam spot) may be calculated and applied to other regions, objects or tissues in the image in order to calculate a distance of such other regions, objects or tissues from the in-vivo device.

When using an endoscope for in-vivo examination, the endoscope may include an actual forceps (endoscopic forceps) which may enable a professional to estimate size of in-vivo objects by opening the forceps' arms to the size of the in-vivo objects.

SUMMARY OF THE INVENTION

Embodiments of the present invention may provide a system and method for size estimation of in-vivo objects, the method including displaying a two-dimensional image of in-vivo objects obtained by an in-vivo imaging device, said image comprising image pixels, receiving an indication of a selected area representing a point of interest from the user, estimating the depth, e.g. the distance of an object from the imaging device, and calculating a three-dimensional coordinates representation of the plurality of image pixels, based on the estimated depths.

Additionally, a method according to embodiments of the present invention includes projecting or casting a virtual tool of a known size onto the three-dimensional representation (e.g., adding the tool to the representation) to determine ending points of the tool. The projecting or casting may include and/or may be performed in order to determine ending points of multiple lengths of the virtual tool. The projecting or casting may include creating a virtual tool having an origin point and multiple extensions extending from the origin point or lengths from the origin point in multiple directions and an origin point from which the extensions extend, and positioning ending points of the multiple extensions or lengths on points defined by three coordinates in three-dimensional space, on the three-dimensional representation, wherein each of the ending points is positioned at a same pre-determined absolute distance in millimeters from the point of interest in the three-dimensional representation. The positioning may include checking the absolute distance from the origin point to multiple points on the three-dimensional representation of the tissue along a certain direction, and if, for a certain point, the absolute distance equals the pre-determined distance, determining the certain point as the position of an ending point.

Additionally, a method according to embodiments of the present invention includes adding or projecting the virtual tool onto the two-dimensional image to create a cursor or other on-screen indication tool having a two-dimensional shape on the displayed image, the cursor having multiple dimensions in different directions, the dimensions end at the determined ending points projected on the two-dimensional image. The projecting may include creating a two-dimensional cursor having multiple projected dimensions in multiple directions, the dimensions end at the determined ending points projected on the two-dimensional image, wherein the projected dimensions are the distances on the two-dimensional image from the ending points, projected on the displayed image, to the point of interest, selected or marked on the displayed image.

Additionally, the cursor according to embodiments of the present invention is movable over the displayed image, while the projected dimensions are changeable dynamically according to the distances on the two-dimensional image from the ending points, projected on the displayed image, to the point of interest, selected or marked on the displayed image, wherein the point of interest is changed as the cursor is moved or repositioned over the displayed image.

A system for size estimation of in-vivo objects according to embodiments of the present invention may include a workstation comprising a memory and a processor, the memory to store an image captured by an in-vivo imaging device. The processor may be configured to: display a two-dimensional image of in-vivo objects obtained by in-vivo imaging device; receive indication of a selected area representing a point of interest from the user via a user input device; calculate a three-dimensional coordinates representation of the plurality of image pixels, based on the estimated depths; cast a virtual tool of a known size onto the three-dimensional representation to determine ending points of the tool; and project the virtual tool onto the two-dimensional image to create a cursor having a two-dimensional shape on the displayed image, the cursor having multiple dimensions in different directions, the dimensions end at the determined ending points projected on the two-dimensional image.

Further, the processor may be configured to: create a virtual tool having an origin point and multiple extensions extending from the origin point in multiple directions or lengths from the origin point in multiple directions that end at said ending points in the multiple directions; and position ending points of the multiple extensions or lengths on points defined by three coordinates in three-dimensional space, on the three-dimensional representation, wherein each of the ending points is positioned at a same pre-determined absolute distance from the point of interest in the three-dimensional representation.

Further, the processor may be configured to: check the absolute distance from the origin point to multiple points on the three-dimensional representation of the tissue along a certain direction; and if, for a certain point, the absolute distance equals the pre-determined distance, determine the certain point as the position of an ending point.

Further, the processor may be configured to create a two-dimensional cursor having multiple projected dimensions in multiple directions, wherein the projected dimensions are the distances on the two-dimensional image from the ending points, projected on the displayed image, to the point of interest, selected or marked on the displayed image.

According to further embodiments of the present invention, a method for size estimation of in-vivo objects includes creating a virtual measurement tool for size estimation of in-vivo objects, the tool comprising an origin point on a point of interest on a displayed two-dimensional image, and multiple lengths from the origin point in multiple directions in a three-dimensional representation of the image of a tissue captured by said in-vivo imaging device, each length having an ending point at a distal end of the length, positioned on a point in the three-dimensional representation of the image, wherein the ending points have the same absolute distance from the origin point in the three-dimensional representation, and projecting the virtual measurement tool on said image, for creating a two-dimensional cursor having multiple projected dimensions in multiple directions, the projected dimensions being the distances on the two-dimensional image from the ending points, projected on the displayed image, to the point of interest, selected on the displayed image.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which.

Figure 1:
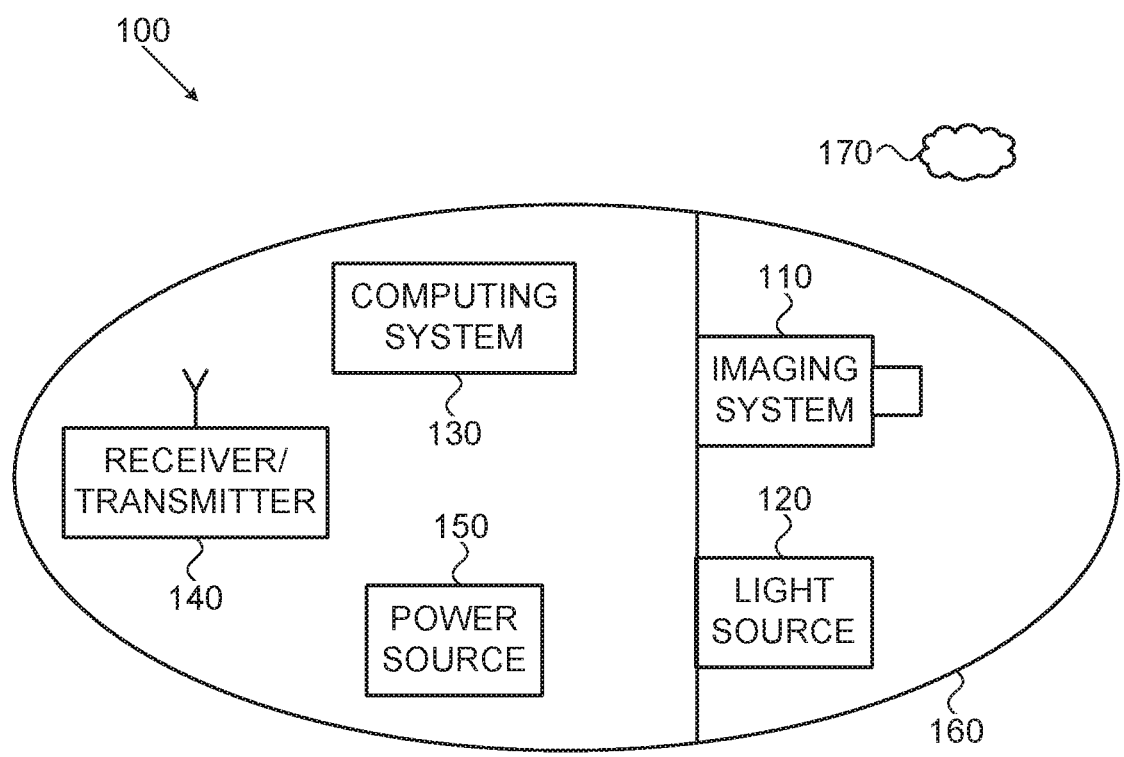
FIG. 1 shows a schematic diagram of an in-vivo imaging device according to embodiments of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed at the same point in time.

Embodiments of the system and method of the present invention may be used in conjunction with an imaging system or device capable of obtaining images of in-vivo objects. More specifically, in some embodiments, any imaging device or system that may be installed in an in-vivo device as described herein may be used. However, it will be understood that embodiments of the invention are not limited by the type, nature or other relevant aspects of the imaging system, device or unit used.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

According to one embodiment, an in-vivo imaging device may collect a series of still images as it traverses the GI tract. The images may be later presented as, for example, a stream or sequence of images or a moving image of the traverse of the GI tract. An in-vivo imaging device or system may collect a large volume of data, as the in-vivo imaging device may take several hours to traverse the GI tract. The in-vivo imaging device may record images at a rate of, for example, four to forty images per second (other rates, such as two frames per second, may be used). The in-vivo imaging device may have a fixed or variable frame capture and/or transmission rate. When the in-vivo imaging device has a variable or adaptive frame rate (AFR), the in-vivo imaging device may switch back and forth between frame rates, for example, based on parameters, such as an imaging device speed, estimated location, similarity between consecutive images, or other criteria. A total of thousands of images, for example, 50,000 images, may be recorded. The image recordation rate, the frame capture rate, the total number of images captured, the total number of images selected if the moving image is edited, and the view time of the moving image, may each be fixed or varied.

The image data recorded and transmitted by the in-vivo imaging device may be digital color image data, although in alternate embodiments other image formats may be used. In one example, each frame of image data may include 320 rows of 320 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in a data processor storage unit (for example, storage 630 in FIG. 2). The stored data may include one or more pixel properties, including color, intensity and brightness.

While information gathering, storage and processing are described to be performed by certain units, the system and method of the present invention may be practiced with alternate configurations. For example, the components gathering image information need not be contained in an imaging device, but may be contained in any other vehicle suitable for traversing a lumen in a human body, such as an endoscope, stent, catheter, needle, etc. A data processor storage unit may store a series of images recorded by an in-vivo imaging device. The images the in-vivo imaging device records as it moves through a patient's GI tract may be combined consecutively to form a moving image stream or video.

An imaging parameter or imaging information as referred to herein may be any information related to or associated with an image. For example, imaging parameters, values or information may be associated with, and obtained from pixels in a digital image as known in the art. Accordingly, it will be understood that any information that may be associated with pixels of a digital image or other imaging representations, e.g., a hue, intensity, color, saturation and the like may be obtained, analyzed and/or processed as described herein. Likewise, an image as referred to herein may typically (but not necessarily) be a digital image or representation of a space or a scene as captured by an imaging device. Embodiments of the invention may base a processing of an image on specific information, parameters or other aspects of the imaging device, e.g., a relation of pixels to size may be determined using a known resolution parameter of the imaging device used for acquiring or digitizing an image. Accordingly, parameters related to the imaging device may likewise be referred to herein as imaging parameters.

According to some embodiments, a distance from an imaging device and/or a size of an object may be determined or estimated by obtaining a tissue model designed to provide at least a mapping of at least one imaging parameter to at least one distance parameter, obtaining, by an imaging system, a digital image of the object, selecting at least one pixel in the digital image, wherein such at least one pixel is associated with the object, e.g., represents at least part of the object in the digital image and calculating, based on the tissue model and data associated with the pixel, a distance parameter related to a distance of the object from the imaging system.

For example, given the distance of an object in an image (e.g., the distance of the object from the imaging system at the time the image was acquired), a relation of the number of pixels associated with the object (e.g., the number of pixels enclosed by an edge or border of the object) with the size of the object may be determined based on known parameters of the imaging system.

Reference is now made to FIG. 1, which shows a schematic diagram of an in-vivo imaging device 100 according to one embodiment of the present invention. As shown, in-vivo imaging device 100 may include an imaging system 110, a light source 120, a computing device 130, a receiver transmitter 140, a power source 150 (e.g., an internal battery or a wireless receiving system) and a viewing window or dome 160. In some embodiments, in-vivo imaging device 100 may be, for example, a swallowable capsule capable of capturing images and/or obtain other data. More specifically, in-vivo device 100 may be configured, designed or otherwise enabled to independently obtain images and further configured to perform at least one of: processing, storing images and other information, communicating images to a remote computing or communication device and/or provide information, data or parameters related to obtained and/or processed images. For example, while inside a body of a human or other living creature, in-vivo device 100 may obtain images of tissues, objects or its surroundings, store, process and/or communicate such obtained images as well as possibly calculate, compute, determine and provide various indications, alarms, results or measurements.

In some embodiments, in-vivo device 100 may be in the shape of a capsule as shown in FIG. 1, including for example a viewing window or dome 160. Viewing window 160 may be convex or substantially convex and smooth, and may project outward from the main body and/or housing of device 100. Viewing window 160 may be designed to provide a suitable field of view (FOV) for imaging system 110 and/or to enable light from light source 120 to reach objects outside device 100, e.g., object 170 as shown. Other shapes may be used, and the device need not be swallowable or a capsule. For example, device 100 may be implanted, inserted or otherwise located in any applicable location.

Imaging system 110 may be any suitable imaging system. For example, imaging system 110 may include any number of lenses or mirrors, support assemblies that may be used to direct imaging system 110 at a specific direction or angle and/or an embedded control module. Imaging system 110 may comprise a complementary metal oxide semiconductor (CMOS) imaging camera. As known in the art, a CMOS imager is typically an ultra-low power imager and is provided in chip scale packaging (CSP). Other types of CMOS or other imagers may be used, e.g., a CCD imager. A 320×320 pixel imager may be included in imaging system 110, e.g., one having pixel size between 5 to 6 microns. According to some embodiments pixels may be each fitted with a micro lens.

Light source 120 may be any suitable light or energy source capable of producing, e.g., periodically or continually, light or other form of energy that may interact with objects outside device 100, e.g., object 170 shown in FIG. 1. For example, light emitted periodically or continually by light source 120 may be reflected from such objects and captured by imaging system 110. For example, light source 120 may be a set of light emitting diodes (LEDs), organic LEDs (OLEDs), or other suitable light sources, may provide light to illuminate objects thus enable acquiring images as known in the art. In other embodiments, other forms of energy or types of light may be produced by light source 120, e.g., any form light or energy that imaging system 110 is capable of acquiring.

Computing system 130 may be any suitable article, processor, chip, controller or suitable computing device suitable for processing images as described herein as well as controlling, coordinating or otherwise manage components in device 100. For example, computing system 130 may perform one or more of: causing imaging system 110 to acquire an image, process the image, cause such image to be stored on a local storage (not shown) in device 100, cause such image to be communicated to a remote device, e.g., by controlling transmitter/receiver 140 and the like. In some embodiments, computing system 130 need not be a separate component; for example, parts of computing system 130 may be integral to, or embedded in, imaging system 110 or receiver transmitter 140. It will be understood that any functionality of computing system 130 may be distributed to any applicable or suitable component of device 100.

Transmitter/receiver 140 may transmit and/or receive images and/or other (e.g., non-image) information to/from a remote device. For example, a computer configured to wirelessly communicate with device 100 may be placed near a patient and may wirelessly communicate with device 100. Transmitter/receiver 140 may be an ultra-low power radio frequency (RF) transmitter with high bandwidth input, possibly provided in chip scale packaging, may be combined with a processing chip or circuit and may transmit and/or receive information via an antenna as shown. Device 100 may include a power source 150, such as one or more batteries. For example, power source 150 may include silver oxide batteries, lithium batteries, or other electrochemical cells having a high energy density, or the like. Other power sources may be used. Other components, modules or units may be used. For example, power source 150 may be capable of receiving power from an external power source transmitting power to the device 100.

Embodiments of device 100 may typically be autonomous and/or self-contained. For example, the device may be a capsule or other unit where components are substantially contained within a container or shell, and where the device does not require any wires or cables to, for example, receive power, obtain, store or transmit information etc. Device 100 may communicate with an external computing or communication system that may receive, process, store, communicate and display images or other data or information received from device 100. Such remote system or device may further be used to control or otherwise interact with device 100. Accordingly, it will be understood that processing of digital images and determining parameters related to distance and/or size as described herein may be performed by a remote computing system configured to receive images acquired by in-vivo device 100.

In some embodiments, some or all of the processing of images as described herein may be performed by device 100, e.g., using computing system 130. In other embodiments, device 100 may perform some of the processing described herein and another computing system, e.g., a remote system may perform other processing or tasks. In yet other embodiments, device 100 may only obtain images, perform limited or no processing of such acquired images and send the images to a remote computing device or system which may perform processing, analyzing and determining of various parameters based on received images, e.g., such remote system may display images to a physician, receive a selection from the physician and, determining a size of an object shown in an image based on the physician's selection.

A storage unit may be worn on the patient's body and may communicate with device 100 to record acquired images. The storage unit may subsequently communicate with a computer, e.g., a workstation or server that may receive such stored images and further process them as described herein, e.g., compute and/or calculate size of objects shown in such images.

Figure 2:
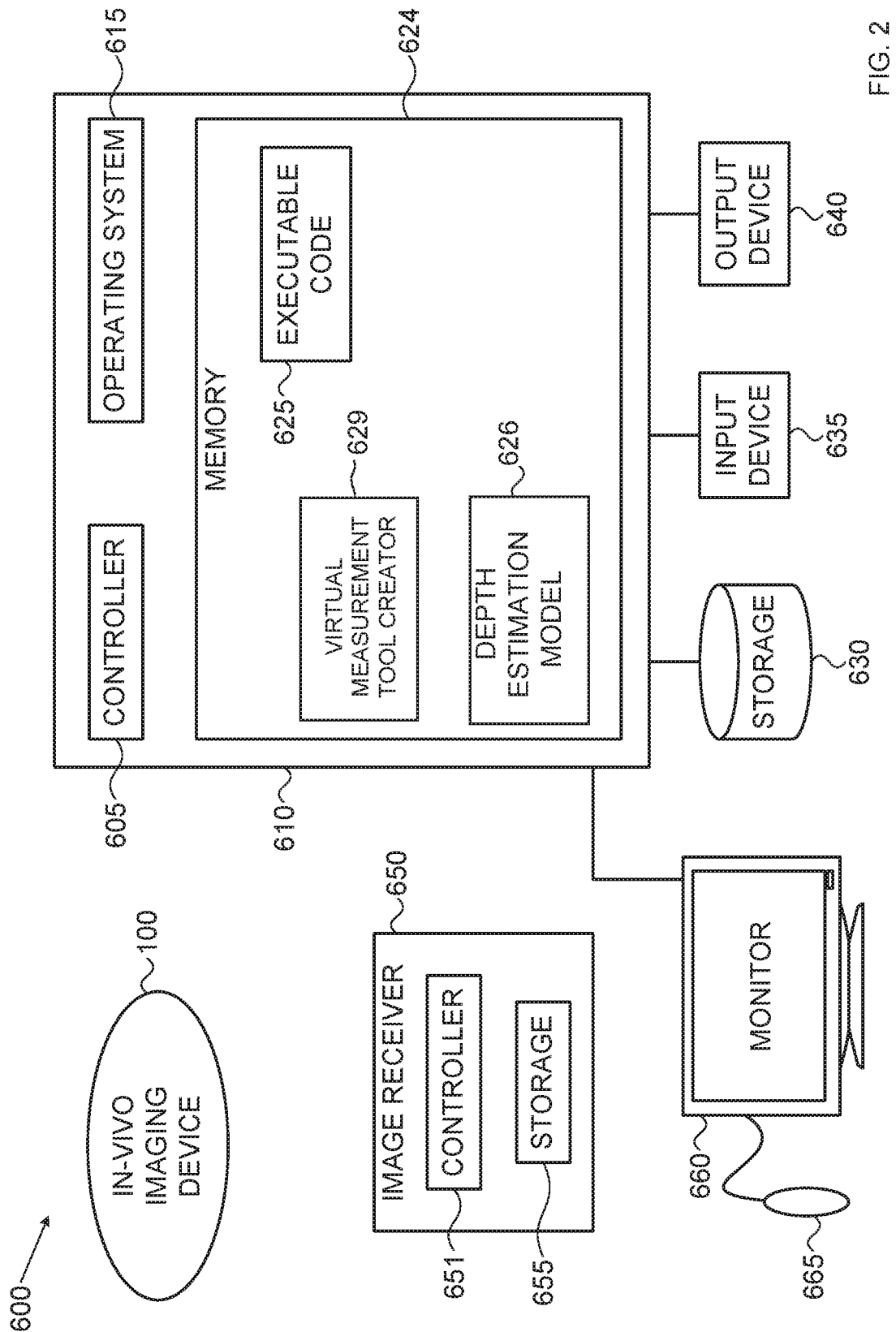
FIG. 2 shows a schematic illustration of an in-vivo imaging system, according to an embodiment of the present invention.

Reference is now made to FIG. 2 that shows a schematic illustration of an in-vivo imaging system 600, according to an embodiment of the present invention. According to some embodiments, system 600 may include an in-vivo imaging device, for example, an in-vivo imaging device 100 as described herein. As described herein, in-vivo imaging device 100 may be a swallowable in-vivo imaging device, but other types of devices or suitable implementations may be used. According to one embodiment, in-vivo imaging device 100 may communicate with an external receiving and display system to provide display of data, control, or other functions. System 600 may include an image receiver 650 including processor or controller 651 and a storage unit 655. For the sake of simplicity, various components that may be installed or included in image receiver 650 are not shown. For example, image receiver 650 may include output and input components or devices that may be similar to input device 635 and an output device 640 and/or an operating system similar to operating system 615, memory similar to memory 624, etc. It will be understood that image receiver 650 may be any suitable computing device and may perform any operations related to estimating or determining a distance, size or other dimensions of an object shown in an image as described herein.

Image receiver 650, which may include an antenna or antenna array, an image receiver storage unit 655 and a data processor or controller may be a small device that may be carried by a patient. For example, an (e.g. ambulatory) patient may wear image receiver 650 on a belt or wrist. Image receiver 650 may communicate, e.g., wirelessly, with in-vivo device 100, receive, from in-vivo device 100, images and store received images on storage 655. Accordingly, image receiver 650 may be attached to or worn on a patient or subject and may collect images obtained by in-vivo imaging device 100 over a relatively long period of time. Image receiver 650 may be configured to communicate, wirelessly or otherwise, with computing system 610 and transfer images and/or other information to computing system 610. For example, images and/or other information received from in-vivo imaging device 100 may be stored on storage 655 and may be transferred from storage 655 to computing system 610, e.g., using wireless communication, a universal serial bus (USB) connection or any suitable mechanism or communication method.

Computing system 610 may analyze, process or otherwise manipulate or handle any applicable images acquired by any suitable imaging device in any applicable environment and/or of any applicable objects. Likewise, according to embodiments of the invention, computing system 610 may compute or derive size estimations of objects or regions in any applicable images. In a particular embodiment, computing system 610 may receive images from in-vivo device 100 or image recorder 650 and may produce a simulated forceps to be displayed on top of the images for estimation of a size of objects in such images. In some embodiments, in-vivo imaging device 100 may perform tasks as described herein with reference to computing system 610. For example, in-vivo imaging device 100 may include some components of computing system 610 as well as possibly, additional components. Accordingly, various operations and tasks that may be performed by computing system 610 may be performed by in-vivo imaging device 100, e.g., by computing system 130 or, in other embodiments, by image receiver 650. In some embodiments, processing of images performed in order to estimate a distance, size or other dimension of an object may be distributed. For example, a first part of the processing may be performed by computing system 130 in in-vivo device 100 and a second part may be performed by system 610. For example, an image may be modified by computing system 130 in in-vivo device 100 according to an illumination model, e.g., values associated with pixels may be altered based on an illumination or optical model which may be device specific. Such pre-processed image may then be communicated to system 610 that may perform a distance, size or other dimension estimation.

Computing system 610 may include a processor or controller 605 that may be, for example, a central processing unit processor (CPU), a chip or any suitable computing or computational device, an operating system 615, a memory 624, a storage 630, an input device 635 and an output device 640. Operating system 615 may be or may include any code segment designed and/or configured to perform tasks involving coordination, scheduling, arbitration, supervising, controlling or otherwise managing operation of computing system 610, for example, scheduling execution of programs loaded into memory 624. In some embodiments, operating system 615 may be a commercial operating system. Memory 624 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 624 may be or may include a plurality of, possibly different memory units.

Executable code 625 may be any executable code, e.g., an application, a program, a process, task or script. Executable code 625 may be executed by controller 605 possibly under control of operating system 615. For example, executable code 625 may be an application designed to analyze an image, to determine the distance of objects in such image from the imaging device used for acquiring the image and to create and display a virtual tool for size estimation of in-vivo objects according to embodiments of the present invention. Controller 605 may be configured to carry out methods according to embodiments discussed herein. Storage 630 may be or may include, for example, a hard disk drive, a floppy disk drive, a Compact Disk (CD) drive, a CD-Recordable (CD-R) drive, a universal serial bus (USB) device or other suitable removable and/or fixed storage unit.

Input devices 635 may be or may include a mouse, a keyboard, a touch screen or pad or any suitable input device. In some embodiments, input devices 635 may be an input port. For example, an input port (e.g., a network interface card (NIC), a USB port or a wireless port or card) may be used to receive images from image recorder 650, in-vivo device 100, or an external storage. It will be recognized that any suitable number of input devices may be operatively connected to computing system 610 as shown by block 635. Output devices 640 may include one or more displays, speakers and/or any other suitable output devices. It will be recognized that any suitable number of output devices may be operatively connected to computing system 610 as shown by block 640. Any applicable input/output (I/O) devices may be connected to computing system 610 as shown by blocks 635 and 640. For example, a network interface card (NIC), a printer or facsimile machine, a universal serial bus (USB) device or external hard drive may be included in input devices 635 and/or output devices 640.

Computing system 610 may be operatively connected to, for example, a monitor or computer monitor 660 and a point and click device 665. According to embodiments of the invention, images obtained by in-vivo device 100 and provided to computing system 610 may be displayed on monitor 660, for example together with virtual simulated forceps as described herein.

As shown, a depth estimation model 626, which may include, for example, a tissue model, and/or an optical model and/or an illumination model, as described in detail herein below, may be loaded into memory 624 (other or different models may be used). Depth estimation model 626 may estimate the distance of an object from the imaging device (or from the imaging system). The estimated depth (or distance) along with the two-dimensional display and the optical model, may translate each pixel of the two-dimensional display to three-dimensional real world coordinates, e.g., to the actual location of the object in three-dimensional space. Depth estimation model 626 may be any suitable code or data, and may be affected by execution by, for example, processor 605 or another suitable processor. In some embodiments, depth estimation model 626 may include a tissue model, an optical model, an illumination model and/or other models. It will be understood that the tissue model, optical model and illumination model discussed herein may be implemented by any applicable construct or module and may be combined or broken into components as known in the art. For example, in one embodiment, these models may be a data structure that may enable an application to search for or determine distance values based on a set of imaging parameters. In other embodiments, depth estimation model 626 may include parameters that may be used by an application in order to derive, determine or estimate a distance of an object depicted in a pixel from the imaging device at the time of capturing the image. In one embodiment, a depth estimation model 626 may be generated based on known optical and/or known illumination characteristics of an imaging device. Depth estimation model 626 may map the distances of objects in the image to create a distance map by executable code 625 and/or depth estimation model 626, which may indicate, for each pixel in an image, the distance of the imaged tissue, represented in the captured image, from the imaging device. A distance map may be calculated for a displayed image and/or may be pre-calculated for some or all images and, for example, may be stored with the image as metadata. For example, an application (e.g., executable code 625) may extract an intensity and color from a pixel in an image, may modify such values, for example based on data in tissue, illumination and/or optical models in depth estimation model 626 and/or may use such modified values as input to depth estimation model 626 in order to estimate a distance of an object (or a portion of an object) represented by the image pixel, from the imaging device.

According to an embodiment of the invention, a tissue model may be generated, obtained and/or provided and used as described herein. Various aspects, traits or qualities of a tissue as related to, reflected in, or represented by a digital image of the tissue may be measured, determined, derived or modeled. As known in the art, a pixel in a digital image may be associated with imaging parameters, values or levels of, e.g., hue, intensity, color, brightness, luminance, chromaticity, saturation levels of such imaging parameters or any other relevant data, parameters or values. Such imaging parameters as related to a tissue or object may be affected by various aspects. In particular, such imaging parameters may be affected by the distance of the object from the imaging device used for acquiring the image. Accordingly, a tissue model may associate, correlate or map one or more imaging parameters, e.g., as reflected by data associated with image pixels, to a distance of the imaged object from the imaging device at the time of capturing the image.

A tissue model may be designed and generated such that it may be suitable for use with any patient and/or any tissue. In other embodiments, a model may be specifically generated or adapted to a specific tissue, patient, patient condition or other relevant aspects. For example, it may be empirically or otherwise determined that tissues in the colon exhibit specific attributes, behavior, response or other aspects or traits related to light and/or imaging. Accordingly, a tissue model may be generated in accordance with such attributes or aspects such that the tissue model may be used in order to process images of colon tissues as described herein. For example, a model generated based on known levels or constants of absorption or reflection of light by a tissue, color and intensity of light emitted from a tissue and possibly, parameters related to a relevant system and environment, may be used to determine or estimate a distance of a tissue segment from the imaging device. In some embodiments, data extracted from pixels in a digital image may be related to a tissue model in order to calculate a distance and/or size of an object or region.

A tissue model may be designed to be specifically adapted or suitable for specific cases, patients, patient condition or illness, etc. For example, a first model may be suitable for young children and a second model may be specifically suitable or adapted for old patients. A tissue model may be related to a condition of a patient. For example, a first tissue model may be used for a patient who was on a normal diet when the images were taken, while a second model may be used for a patient who was made to abstain from food for twenty four hours, or made to drink a large amount of liquids prior to the images being taken. In some embodiments, a base or universal model may be modified according to relevant aspects. For example, a base or universal model may be modified based on the imaging system used or aspects related to the light used, e.g., intensity or color composition of light emitted by light source 120. In yet other embodiments, a tissue model may be specific to a region or anatomical organ in a body.

For example, a tissue model may be generated for the colon or gastrointestinal (GI) tract. A tissue model may represent or exhibit attributes of real tissue as reflected in a digital image. A tissue model may likewise symbolize, describe, stand for, contain, or be based on, imaging parameters of a real tissue and the medium between the imaging device and the tissue, such as, for example, the in vivo fluid. For example, an interaction of a tissue with light may be known, e.g., spectral characteristics of a given light that is made to be reflected from the tissue may be studied or determined and represented by a tissue model. Likewise, an amount or percentage of light reflected from a tissue, or imaging parameters related to the intensity, per color intensity, hue, luminance, chromaticity or brightness of light reflected and/or absorbed by a tissue may be studied, determined and/or known. For example, by examining a series of images obtained using known relevant parameters such as any relevant parameters related to the light used, the tissue being imaged, the distance of the tissue from the imaging device and the optical and illumination aspects or characteristics, a model of the tissue may be generated or constructed. In some embodiments, an image may be analyzed, various aspects may be determined, and a tissue model may be selected or generated dynamically and/or automatically.

A tissue model may include a mapping of imaging or other parameters to a distance or other relevant parameters. Accordingly, a tissue model may be used to map, correlate or associate one or more imaging or other parameters, values or other data in an image to a distance or a size. For example, given relevant parameters related to light reflected from a tissue as described herein are known and the relevant optical and illumination aspects or characteristics are known, a color and/or intensity of a tissue segment or an object as reflected by an image may be mapped to a distance of the tissue segment or object from the imaging system used for obtaining the image.

Various combinations of parameters that may be extracted from, or computed based on, an image may be likewise mapped. For example, a level of absorption or reflection of only part of the light spectrum may be examined and/or mapped as described herein. In one particular embodiment, a tissue model may analyze only red light reflected from a tissue. Red light may be light detected only in a red color channel of an imager, where each of the red, blue and green color channels detects light in a wide range of wavelengths centered about wavelengths in the red, blue and green color ranges, respectively. In one example, the red color range includes light having wavelengths in a range of 600-750 nanometers (nm). A tissue model may map the intensity of light reflected from a tissue (e.g., the colon) and detected by the red channel (or red pixel sensors) of the imager, to a distance. For example, assuming light traveling is attenuated according to a reciprocal relation or function of distance, a distance of an object may be determined by the equation: $D = A + B/\sqrt{R}$, where D is the distance of the object from the imaging device at the time the image was acquired, A and B are constants selected as described herein and R is the intensity of red light.

In generating a tissue model, any method of mapping, associating or correlating one or more imaging parameters such as an intensity or color of light to a distance may be used. For example, using an image in which the distance of objects from the imaging system is known, a human may manually map colors of a known tissue to distance to generate a tissue model (the use of the tissue model, as discussed herein, is automated). In other embodiments, extrapolation, adaptation, image analysis or other methods or techniques may be used in order to automatically map various parameters in an image to a distance such that a mapping, association or correlation of imaging parameters to distance is realized.

An illumination model may represent any relevant illumination parameters or aspects related to an acquisition of an image. An illumination model may include, but is not limited to, the level or intensity of illumination or luminance emitted (e.g., by a light source such as light source 120) and/or absorbed or reflected (e.g., by a medium and/or tissue). For example, an illumination model may define aspects related to parameters such as color intensity, hue, color saturation, luminance, chromaticity, brightness of light may be used in order to compile, generate, produce or obtain an illumination model. For example, such parameters related to an environment in which images are acquired, e.g., the medium through which light travels before being captured by an imaging device may be used in generating an illumination model. Likewise, parameters related to an irradiation or light source, e.g., the wavelength and/or intensity of light being emitted by a light source may be known and accounted for in an illumination model. A light source may be fitted with lenses, minors or various diffractive or other optic elements. Accordingly, an illumination model may be generated such that any relevant effect of such lenses or elements is taken into account. An illumination model may be based on, or in accordance with, illumination sources, lenses and other components, their respective usage, type and attributes or any other parameters that may be pertinent to illuminating or imaging tissues or objects.

In other embodiments, an illumination model may be based on the specific device or system used for acquiring the relevant image. For example, the central point in an image may be illuminated more brightly than points located near the edge of the image. Such difference in illumination level or other parameters may result from the shape or other characteristics of the illumination sources, their location in a device, etc. In some embodiments, an illumination model may eliminate such differences, calculate calibrating parameters or otherwise take any such optical, illumination or other aspects into account. The calibrated parameters of the illumination model may be the same for all (or all of a set, model or series) imaging devices or may be calibrated specifically for each device, for example, using programmable parameters. An illumination model that describes illumination differences or inhomogeneity may be defined with respect to a reference geometry or plane. For example, the reference geometry may be a sphere at radii r1 . . . rN centered about the imaging device. In some embodiments, the optimal illumination model may vary as the distance varies between the imaged object and the illumination source or imaging device. Some embodiments may use an average or most often optimal illumination model or may iteratively select and switch to the optimal illumination model for each image or image stream segment.

According to embodiments of the invention, an optical model may be used in order to process and/or analyze an image. An optical model as referred to herein may be or may be generated based on distortion in the image. For example, light acquired by an imaging system may travel through a medium (e.g., a dome or window in in-vivo device 100) and may bend non-uniformly through the medium due to optical variations therein. An optical model may include parameters or coefficients related to magnification distortion, radial distortion, or other types of distortion, for example, to account for and correct such distortion in the images. For example, an optical model may include reflection, refraction, diffraction or other optical distortion coefficients or parameters. Lenses or minors used by an imaging device may cause specific distortion effects throughout all the images the device captures. Additionally, distortion effects may be introduced as a result of the design, shape and other aspects of viewing window 160, as well as the medium through which light travels when exiting device 100. Such aspects may be accounted for in an optical model and may, accordingly, affect a mapping of imaging parameters to a distance.

An optical model may take any such aspects into account and may be used in order to correctly or better map imaging parameters to a distance as described herein. For example, an optical model may be used in order to derive one or more constants or coefficients that may be used to adjust a base tissue model to a specific environment or circumstance. For example, a first optical model may be generated for a first in-vivo device 100 having a specific imaging system, viewing window and light source and a second optical model may be generated for a second in-vivo device 100 having a different imaging system, viewing window and/or light source. Accordingly, a base tissue model may be adapted to a specific circumstance or device based on an optical model. In other cases and as described herein, an optical model may be used to modify imaging parameters or values, e.g., prior to using a tissue model in order to estimate a distance as described herein. In some embodiments, calibration or configuration parameters of the imaging system and/or environment may be used in order to derive an optical model. For example, a direction of light source 120 with relation to imaging system 110 or the type and number of lenses or minors used by imaging system 110 may be observed when generating an optical model. Accordingly, an optical model may represent any optics related aspects of the equipment and environment relevant to an acquisition of images by an in-vivo device and may thus be used in order to correctly map imaging parameters to a distance as described herein.

Accordingly, for example, an illumination model may dictate that a level or percentage of red color extracted from a pixel is to be modified by a certain factor. For example, based on information related to the light source used by in-vivo device 100 when the relevant image was obtained it may be necessary to perform such modification prior to estimating a distance from the imaging device, for example from the imaging system 110 (shown in FIG. 1), for example in millimeters, using depth estimation model 626. In another case, based on information or parameters related to lenses or minors used when acquiring an image, an optical model may dictate that an intensity of light associated with the pixel is to be reduced by a certain factor, for example of 0.98. For example, if depth estimation model 626 was designed to provide an estimation of distance (e.g., depth) of an object from the imaging device based on a specific light intensity of light source 120, when using a different (e.g., weaker) light source, an adaptation may be required in order to produce adequate results.

In yet another embodiment, depth estimation model 626 may be an executable code. For example, an optical model and/or illumination model may be an executable code that may be provided with input in the form of a color and intensity and may provide output in the form of modified values of color and intensity as described herein. Likewise, depth estimation model 626 may be an executable code tissue model that may receive a set of imaging parameters, e.g., a color and intensity and may return as output distance (e.g., depth) estimation. It will be understood that FIG. 2 shows an exemplary schematic illustration of an in-vivo imaging system and that other embodiments or implementations are possible. For example, some or all of the modules of depth estimation model 626, such as a tissue model, optical model and/or illumination model, may be implemented in hardware (e.g., by an application-specific integrated circuit (ASIC) or a chip) or they may be implemented in firmware, e.g., in order to increase speed of operation.

A virtual measurement tool may be a graphical depiction which may be displayed on or overlaid over an image such as an image of tissue to allow a viewer or a processor to estimate or calculate tissue size of an object which appears in the image. In some embodiments, the virtual measurement tool may be used to imitate endoscopic forceps when used by a professional to estimate sizes of in-vivo objects. In contrast to the use of endoscopic forceps for estimation of sizes, the virtual measurement tool may use some objective parameters to estimate the distance of the objects from the imaging device, such as illumination and/or color parameters that have pre-calculated correlation with distances of in-vivo objects. Such parameters and correlations may be stored in depth estimation model 626 and may be used for estimation of distances as described herein.

Virtual measurement tool creator (e.g., a virtual forceps creator) 629 may also be loaded into memory 624. Virtual measurement tool creator 629 may be an executable code and may, for example, be embedded in, initiated by, and/or exchange data with, executable code 625, and/or may be an executable code function that may be called by executable code 625. Controller 605 may be virtual measurement tool creator 629 in that controller 605 may be configured to execute code to perform the functions of virtual measurement tool creator 629.

Based on the distance map created by depth estimation model 626, and based on the relative locations of the pixels of the displayed image, a three-dimensional representation of the displayed image may be created, wherein each pixel of the displayed image may be translated to three-dimensional real world coordinates in millimeters such as, for example, X, Y, Z coordinates or any other suitable set of coordinates in a three-dimensional space, which may represent the real three-dimensional locations relative to the imaging device of points on the tissue represented by the image pixels, at the time of capturing the image. Virtual measurement tool creator 629 may create a virtual measurement tool that may be displayed, for example, as a cursor, on-screen graphic symbol or other display on a displayed image of a tissue. The cursor may have a projected two-dimensional shape, having projected dimensions or lengths extending in multiple directions around an origin point which may be selected or marked, for example by a user or processor, on a point or an area of interest in the displayed image. Each of the multiple projected dimensions or lengths in the multiple directions represents a constant and equal virtual absolute length from the origin point of the tool in the three-dimensional representation of the image, e.g., all the projected dimensions or lengths in the multiple directions of a cursor may represent the same constant pre-determined virtual absolute length that does not change during the examination from the origin point which may be positioned or selected on a point of interest in the displayed image.

It is generally known that objects which are located further from the imaging device appear to be smaller than objects that are located near the imaging device. An imaged scene typically includes a plurality of objects which are positioned at different distances from the imaging device at the time of capturing the image (e.g., in vivo tissue which is imaged may have one portion located near the imaging device, and other portions located further from the imaging device in the same imaged scene). Therefore, although the cursor's projected dimensions or lengths from the origin point in the multiple directions represent a constant and equal length from the origin point in the multiple directions, they may have different displayed dimensions or lengths and may appear non-equal on the displayed image. In some embodiments, the virtual absolute length may be set by a user, for example, according to the expected and/or estimated size of in-vivo objects to be inspected. For example, the projected dimensions or lengths in the multiple directions may represent a length l, for example in millimeters, so that the maximal size of the cursor along one axis from one end of the cursor to another end of the cursor may possibly be 2*l* (as described in detail herein, for example with reference to FIG. 3). For example, the cursor may be designed as an asterisk having 8 arms, e.g. four couples of arms, wherein in each couple of arms, the arms point to opposite directions along one axis, radially from the point of interest which may be a meeting point for the arms. However, the cursor may include any other suitable number and/or arrangement of arms, or may include any other shape with multiple pre-determined directions. In some embodiments, the cursor need not necessarily include arms, for example, the cursor may be shaped as a closed curve, defined by the different lengths or dimensions from the point of interest in the different directions. Any other shape or symbol may be used to create the cursor, and in some embodiments, the user may select or configure the shape according to personal preferences. The directions, for example, to which the arms point or in which the lengths extend may be constant or may be changeable, e.g., by a user. For example, the length l may be set by a user, for example, according to the scope of sizes of the inspected objects in the image. In one example, the length may be set to 5 millimeters.

The cursor or on-screen graphic symbol according to embodiments of the present invention may be placed so that the point of origin is located on any point of interest chosen by a user on a displayed image of in vivo tissue, so that the origin point is at a selected area on the image, for example, a selected pixel or a cluster of pixels on the image, e.g., a pixel or area chosen by a user, for example, by a mouse cursor positioning and/or clicking on the image or by another input device 635 or 665.

As explained, a map of distances may be calculated for the displayed image, so that each pixel of the image may have a distance from the imaging device, calculated by depth estimation model 626. Therefore, each pixel of the displayed image of a tissue may be translated to three-dimensional coordinates, such as, for example, X,Y, Z coordinates in a three-dimensional space or any other suitable set of three-dimensional coordinates. As explained in more detail with reference to FIG. 3, the cursor or on-screen graphic symbol may be virtually projected (e.g., added to the image) on the imaged tissue, with the origin point at a certain three-dimensional location on the imaged tissue, according to the calculated distance of the point represented by the selected pixel or area relative to the imaging device, and based on the relative location of the pixel or area on the displayed image. The projected cursor may terminate at each of multiple directions at an ending point on the imaged tissue, each having the constant virtual length l from the origin point. That is, each ending point may have three dimensional coordinates according to the calculated distance and the direction of this point from the imaging device at the time of capturing the image, calculated by depth estimation model 626, so that the distance from the origin point to each of the ending points is equal to the virtual length l. When projected on the displayed image, the tool may have in each of the multiple directions a projected dimension or length on the two dimensional displayed image, according to the projection of the length l on the displayed image at each direction. This effect may enable a user, or a processor, to make an immediate and/or intuitive estimation of sizes and/or shapes of imaged in-vivo objects. In some embodiments, the size l may be about 4.5 mm to match the size of standard medical forceps. However, the invention is not limited in that respect.

According to some embodiments of the present invention, processor/controller 605 may receive an image of in-vivo objects obtained by in-vivo imaging device 100 (e.g., a two-dimensional image made up of pixels). The image may be displayed, for example, on monitor 660. Processor/controller 605 may then receive an indication from a user about a pixel or area (e.g., a selected pixel or a cluster of pixels) representing a point of interest on the image (the point of interest corresponding to a real world in-vivo feature) or located in an area of interest, for example via input device 635 or 665. Then, according to embodiments of the present invention, the illumination intensity values of the image may be corrected, for example, by an illumination model of depth estimation model 626. Depth estimation model 626 may correct the illumination intensity values by the illumination model, for example, by using a pre-calibrated illumination map that may unify the illumination level through the entire spherical field of view captured by device 100. Depth estimation model 626 may then estimate, for example by the tissue model, the depth of a plurality of image points, e.g. pixels, around the point of interest or pixel, for example pixels covering a certain predetermined area around the selected pixel/area, by converting the corrected illumination intensity values to depths. Based on the estimated depths, the relative locations of the pixels on the image and the optical model describing the optics distortion of device 100, depth estimation model 626 may calculate the three-dimensional coordinates of the plurality of image points. Thus, for example, based on the estimated depths, a three-dimensional representation or three-dimensional coordinate representation (e.g., including three-dimensional coordinates or representing the points as three-dimensional coordinates) of the imaged tissue may be created. Then, virtual tool creator 629 may cast or project a virtual tool of a known or predetermined size, for example, created as described with reference to FIGS. 3 and 4A-4C, onto the three-dimensional representation of the imaged tissue, as described in detail herein (e.g., add the tool to the representation or image). Then, the virtual tool may be projected onto (e.g., displayed on) the two-dimensional pixelated image and created or generated as, for example, a cursor or an on-screen graphic symbol having a two-dimensional shape on the displayed image of a tissue. As explained with reference to FIGS. 3 and 4A-4C, after the positions of ending points of the virtual tool are determined in the three-dimensional presentation of the tissue, the ending points may be projected on the two-dimensional displayed image, to the pixels representing these points on the tissue. Based on these projected points, a cursor or another on-screen graphic symbol may be created and displayed, for example, by drawing different projected dimensions or lengths in different directions of the cursor or on-screen graphic symbol, the dimensions or lengths ending at the projected points.

Accordingly and as described herein, embodiments of the invention may include an article such as a computer or processor readable medium, or a non-transitory computer or processor storage medium, such as, for example, a memory, a disk drive, or a USB flash memory, encoding, including or storing instructions, e.g., computer-executable instructions, which when executed by a processor or controller, carry out methods disclosed herein. For example, a system may include a non-transitory storage medium such as memory 624, computer-executable instructions such as executable code 625 and a controller such as controller 605. Some embodiments may be provided in a computer program product that may include a machine-readable medium stored thereon instructions, which may be used to program a computer, or other programmable devices, to perform methods as disclosed herein.

Other embodiments of the invention may be or may include a system for estimating a distance, size or other dimension of an object imaged by an in-vivo imaging system. The system may include a workstation or any other suitable computing device comprising a memory and a processor. The memory may be configured to store an image captured by an in-vivo imaging system, and the processor may be configured to select at least one pixel in the image, where the pixel is associated with the imaged object. The memory may store a tissue model, an optical model and an illumination model. The processor may be configured to calculate, based on a tissue model (and/or an optical model and/or an illumination model) and data associated with the pixel, a distance parameter related to a distance of the object from the in-vivo imaging system at the time of capturing the image, wherein the tissue model is designed to provide at least one mapping of at least one imaging parameter to at least one distance parameter. As known in the art, a pixel in a digital image may be associated with imaging parameters, values or levels of, e.g., hue, intensity, color, brightness, luminance, chromaticity, saturation levels of such imaging parameters or any other relevant data, parameters or values. Such imaging parameters as related to a tissue or object may be affected by various aspects. In particular, such imaging parameters may be affected by the distance of the object from the imaging device used for acquiring the image. Accordingly, a tissue model may associate, correlate or map one or more imaging parameters, e.g., as reflected by data associated with pixels, to a distance. For example, the processor to select a pixel, calculate a distance parameter related to a distance of the object from the in-vivo imaging system or calculate a size or other dimension of the object may be controller 651 or controller 605 or it may be included in computing system 130 or computing system 610. Based on the calculated distances, the processor may create the virtual forceps cursor or on-screen graphic symbol described herein.

In some embodiments the tasks of estimating a size, distance or other dimensions or parameters related to an object captured or imaged by an imaging system or device such as in-vivo imaging device 100, and/or the task of creating the virtual measurement tool as described herein, may be distributed among a number of controllers, processors or computing systems. For example, computing system 130 and controllers 605 and 651 may jointly perform any computational tasks or calculations in order to estimate a distance and/or size of an object as described herein. As described herein, computing system 130 and controllers 605 and 651 may communicate or exchange (e.g., over wireless or wired links) any data, parameters or information. Computing system 130 and controllers 605 and 651 may collaborate efforts and computational resources in performing any relevant tasks or methods described herein.

Figure 3:
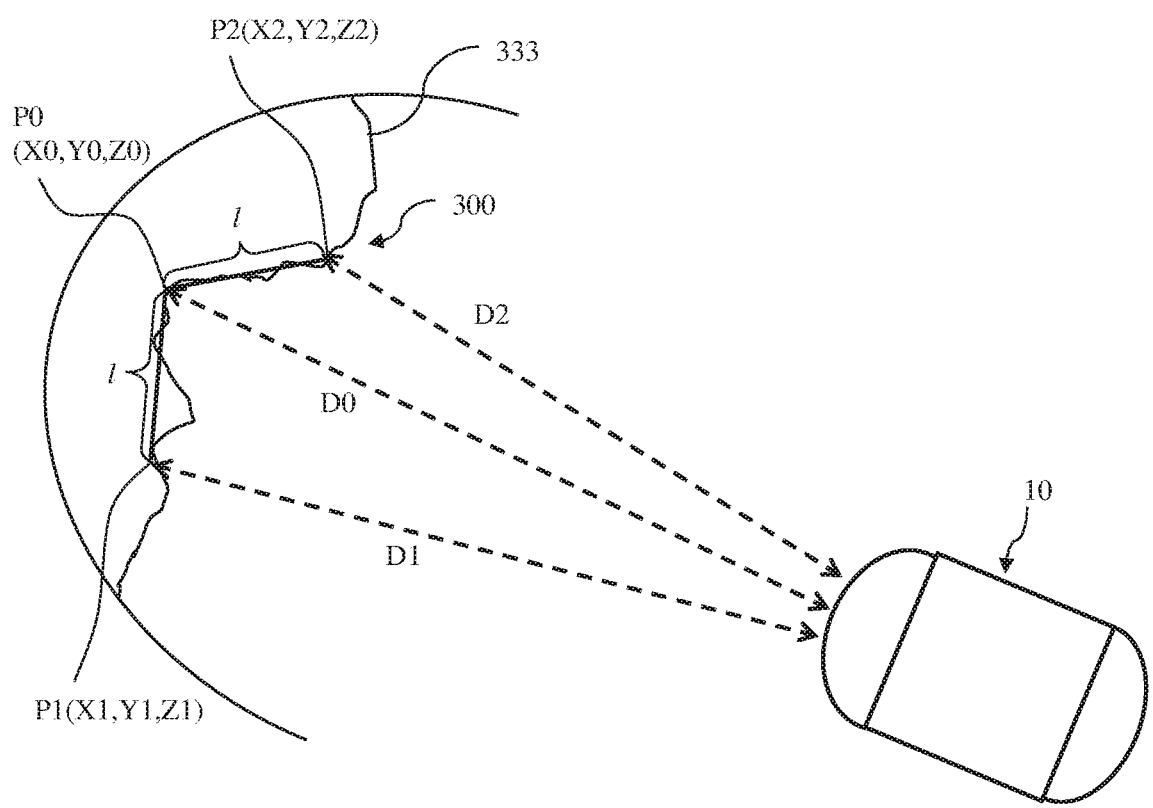
FIG. 3 is a schematic cross-sectional illustration of a virtual tool being cast on a cross-sectional illustration of a three-dimensional presentation of an imaged tissue, for example as may be calculated by a depth estimation model according to embodiments of the present invention.

Reference is now made to FIG. 3, which is a schematic cross-sectional illustration of virtual tool 300 being cast or projected on a cross-sectional illustration of a three-dimensional presentation of an imaged tissue 333, for example, as may be calculated by depth estimation model 626 according to embodiments of the present invention. Virtual tool 300 may include an origin point P0 and extensions of identical length l in different directions, terminating at ending points P1 and P2. As discussed herein, the processor 605 according to embodiments of the present invention may calculate for each pixel in an image a distance value, for example in millimeters, of the tissue represented by the pixel from the imaging device. Based on the distance calculation, the processor 605 may create a virtual measurement tool having multiple extensions or lengths in different directions, extensions or arms in multiple directions and an origin point from which the extensions or lengths extend, or a meeting point from which the arms project, e.g., radially. In some embodiments, virtual tool 300 may have a shape of a circle having a fixed radius of length l, like a circled sheet or cloth, which takes shape of the three-dimensional representation surface when placed on it, so that in each direction, the virtual tool has the same length l. In this case, multiple ending points such as P1 and P2 that may be determined as described herein may create a closed contour along the edge of the circled virtual tool. This closed contour may be projected on the two-dimensional image and create a closed shaped cursor or on-screen graphic symbol as described herein.

Distances D0, D1 and D2 are the distances from imaging device 10 of origin point P0 and ending points P1 and P2, respectively, when tool 300 is virtually placed on the imaged tissue in the three-dimensional representation. The cursor according to embodiments of the present invention (such as cursor or on-screen graphic symbol 310, 310a or 310b shown in FIG. 4A, 4B or 4C) may be positioned on a certain area on the displayed image, for example an area chosen by a professional or user as an area that requires inspection. In one example, a user may position the cursor or the graphic symbol of the virtual measurement tool on or near an area that appears abnormal in the displayed image, or an area suspected as ill or abnormal according to other parameters and/or examination. The cursor may be moved upon a displayed image, for example, by the system (e.g., controller 651 and/or 605 described above) after receiving movement commands from a controlling user interface such as a mouse or keyboard or another suitable user interface and/or may be automatically moved across the image, for example, by the processor/controller 651 and/or 605 described above. When a point of interest is chosen and/or origin point P0 is placed on the point of interest in the three-dimensional representation of the tissue, for example, having the three-dimensional coordinates (X0,Y0,Z0), each of ending points P1 and P2 should be positioned on points on the three-dimensional representation of the imaged tissue, for example having the three-dimensional coordinates (X1,Y1,Z1) or (X2,Y2,Z2), respectively, at an absolute distance l from the point of interest on which P0 is placed, in the three-dimensional representation. E.g., each of the ending points is positioned at a same absolute distance from the point of interest in the three-dimensional representation. Therefore, in order to set or determine the positions of ending points P1 and/or P2 in the three-dimensional representation of the imaged tissue, processor/controller 605 and/or virtual measurement tool creator 629 (controlled, for example, by processor/controller 605) may evaluate or check the absolute distance from the origin point at (X0, Y0, Z0) to multiple points along a certain direction, represented by their three-dimensional coordinates. If, for a certain point, the absolute distance equals the pre-determined distance, the certain point may be set or determined as the position of an ending point. In case the absolute distance from the origin point at (X0, Y0, Z0) to a certain point equals the predetermined length l, the point may be set or determined as the position of an ending point such as P1 or P2.

After the positions of ending points P1 and P2 are determined in the three-dimensional presentation of the tissue, they may be projected on the displayed image, to the pixels representing these points on the tissue. Accordingly, processor/controller 605 and/or virtual measurement tool creator 629 may create a cursor such as, for example cursor 310, 310a or 310b shown in FIG. 4A, 4B or 4C, that may have multiple dimensions, lengths or arms extending in multiple directions, which are the distances from the projections of ending points P1 and P2 on the displayed image to the location of P0 on the displayed image, i.e., at the selected pixel or area representing a point of interest.

Figure 4A:
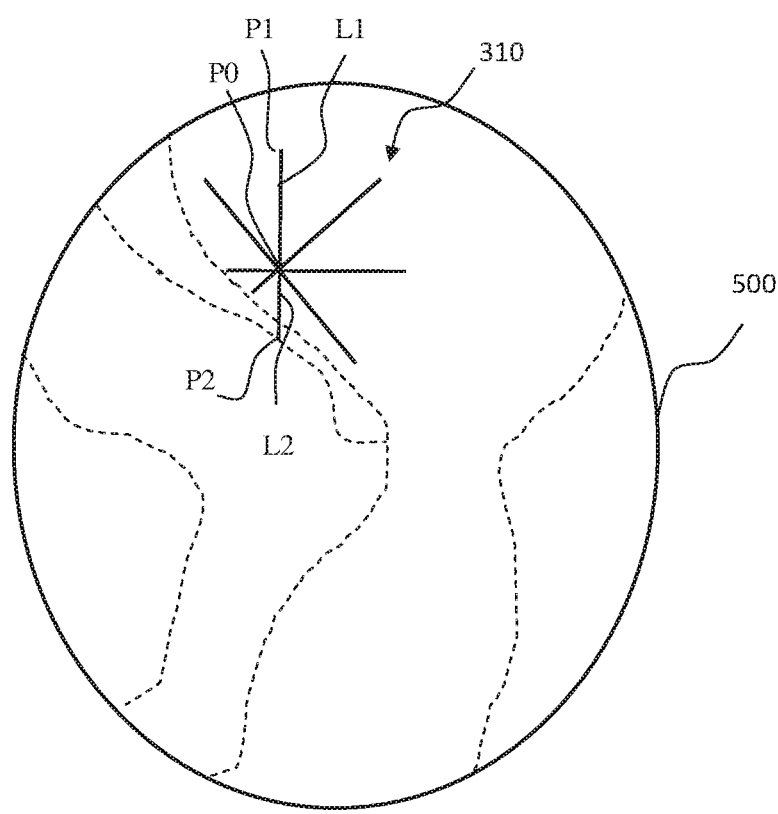
FIGS. 4A, 4B and 4C which are schematic illustrations of a displayed image, for example captured by an in-vivo device, and a virtual measurement tool displayed upon the image, according to embodiments of the present invention.
Figure 4B:
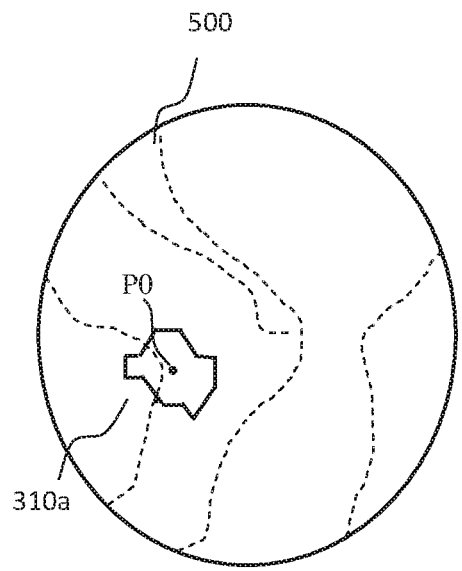
Figure 4C:
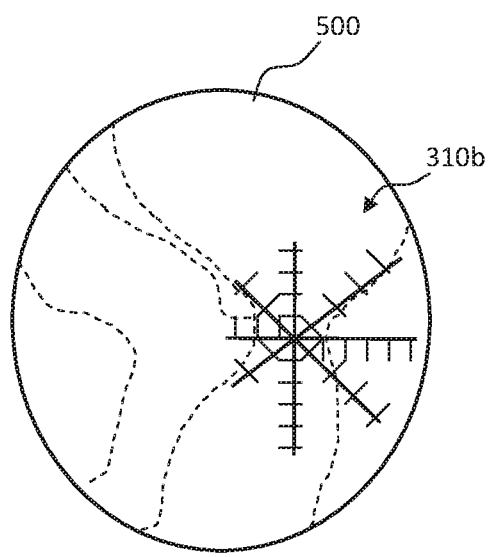

Reference is now made to FIG. 4A, which is a schematic illustration of a displayed image 500, for example captured by an in-vivo device 100 as described in detail above, and a cursor 310 displayed upon or overlaid on image 500, according to embodiments of the present invention. For example, in the illustration of FIG. 4A, two of multiple virtual arms of tool 310, pointing at opposing directions, may have projected dimension or length L1 and L2, respectively, ending at the projected ending points P1 and P2 at distal ends of the arms, respectively. The absolute distance of points P1 and P2 on the three-dimensional representation of the tissue from the origin point P0 equals the predetermined length l, as shown in FIG. 3. As described in detail above, in order to determine the positions of ending points P1 and/or P2, processor/controller 605 and/or virtual measurement tool creator 629 (controlled, for example, by processor/controller 605) may evaluate or check the absolute distance on the three-dimensional representation of the tissue from the origin point P0 to multiple points on the three-dimensional representation of the tissue along a certain direction. FIGS. 4B and 4C illustrate schematically different embodiments of the cursor according to embodiments of the present invention. For example, cursor 310b in FIG. 4B is another configuration of a cursor having multiple different dimensions or lengths or arms in multiple different directions (e.g., in different directions, the length or size of the cursor may differ) as described herein according to embodiments of the present invention. For example, in some embodiments, a cursor may include scale marks along the dimensions or lengths or arms as shown in FIG. 4C. Each of the dimensions or lengths, or lengths of the arms, can be different and/or is typically different, but need not be. Other configurations of cursors are possible according to the various embodiments of the present invention and the invention is not limited to the specific configurations shown in the drawings.

Image 500 and virtual tools/cursors 310, 310a or 310b may be displayed, for example, on a display screen. Virtual measurement tool 310, 310a or 310b may be displayed upon or over image 500, and may have multiple arms or dimensions or lengths and origin or meeting point P0 from which the arms or lengths extend radially. As discussed herein, the multiple arms or lengths may virtually represent a constant and equal absolute length, each arm or length may take on and/or set to a projected length according to the distance from origin point P0 to an ending point of the arm or length in the three-dimensional representation, for example according to embodiments of the invention described herein.

Ending points P1 and P2 may be points on the displayed tissue at which the arms end when virtual measurement tool 310, 310a or 310b is positioned, displayed in or overlaid on a certain area on displayed image 500. As the virtual measurement tool moves upon or across displayed image 500, for example by receiving movement commands from a controlling user interface and/or by the processor/controller moving the tool automatically across the image, the processor 605 or 651, according to embodiments of the present invention, may dynamically change the projected dimensions or lengths or arms of tool 310 as shown in FIGS. 4A, 4B, and 4C, according to the projected distance of the corresponding ending points from the origin point as described herein. In the example of tool 310a of FIG. 4B, the area defined by the contour of tool 310a displayed on the tissue may be a known, fixed absolute area, for example, calculated by determining a fixed radius from the origin point marked by a user in the three-dimensional presentation of the tissue. The outline, circumference, contour or border marked by tool 310a may be determined using the same method as determining the ending points of tool 310 described above.

In some cases, the cursor may have no dimension or length or arm in a certain direction, for example, due to inability to calculate depths or distances in a certain area of the image, for example, due to darkness or lack of clarity of the image in this area, or in cases the cursor is placed near the margins of the image, or in areas where the tissue is abnormal, or where it is covered by content. In some cases, if the selected point of interest is in an area of where depths or distances cannot be calculated, for example, due to darkness or lack of clarity in this image area or portion, virtual measurement tool creator 629 (controlled, for example, by processor/controller 605) may look for at least two ending points in opposite sides of the selected point of interest, having a distance 2$l$ between them, as if the three-dimensional surface is flat and each ending point is at a distance equal to the predetermined length $l$ from the selected point of interest. Thus, a cursor of known size 2$l$ is created on the two-dimensional image, for estimation of sizes of objects in the image by estimating sizes relative to the known size 2$l$.

Figure 5:
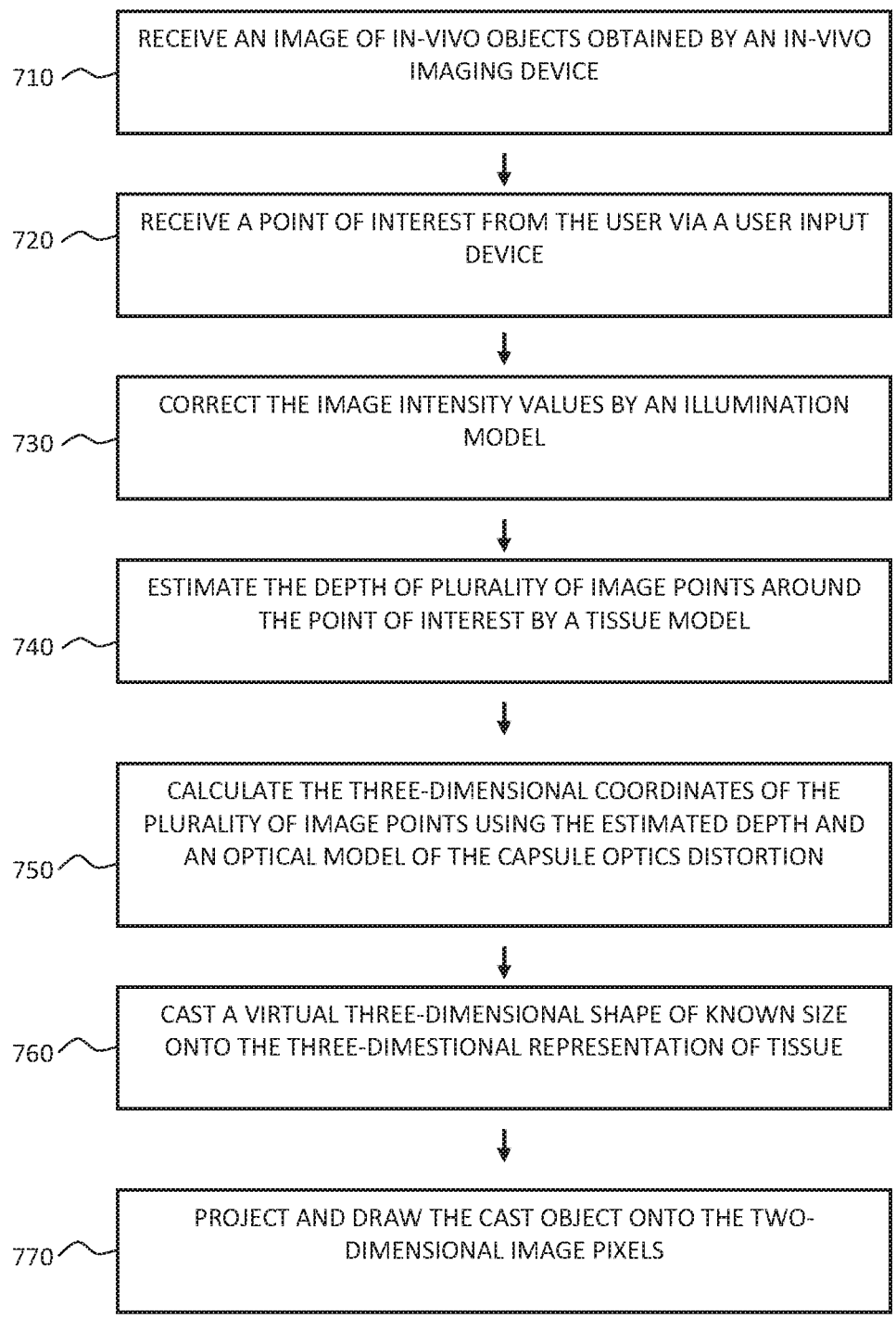
FIG. 5 is a flowchart illustrating a method for size estimation of in-vivo objects according to embodiments of the present invention.

Reference is now made to FIG. 5, which is a flowchart illustrating a method for size estimation of in-vivo objects according to embodiments of the present invention. As indicated in block 710, the method may include receiving an image of in-vivo objects, for example, obtained by in-vivo imaging device 100. The image may be displayed, for example, on monitor 660. As indicated in block 720, the method may include receiving indication of a pixel representing a point of interest from the user via a user input device such as, for example, input device 635 or 665 in FIG. 2, for example, a mouse manipulating a cursor or any other suitable pointing method and/or device. The point of interest may be, for example, a point in an image corresponding to a real-world in-vivo feature. As indicated in block 730, the method may include correcting the illumination intensity values of the image, for example, by an illumination model that may be included in the depth estimation model 626. Depth estimation model 626 may correct the illumination intensity values by the illumination model, for example, by using a pre-calibrated illumination map that may unify the illumination level through the entire spherical field of view captured by device 100. As indicated in block 740, the method may include estimating by the tissue model the depth of a plurality of image points, e.g., pixels, around, near or immediately surrounding the point of interest, by converting the corrected illumination intensity values to depths. As indicated in block 750, the method may include calculating the three-dimensional coordinates' representation of the plurality of image points, based on the estimated depths, the relative locations of the pixels on the image and the optical model describing the optics distortion of device 100. Thus, for example, a three-dimensional representation of the imaged tissue may be created. As indicated in block 760, the method may include projecting or casting (e.g., adding to) a virtual tool of a known size onto the three-dimensional representation of the imaged tissue. As indicated in block 770, the method may include adding or projecting the virtual tool onto the two-dimensional pixelated image and drawn as, for example, a cursor or another on-screen graphic symbol having a two-dimensional shape on the displayed image of a tissue, so that the resulting cursor or on-screen graphic symbol is displayed to the user on top of the displayed image. The virtual tool and pixelated image may be displayed on, e.g., monitor 660, or another display device.

According to some embodiments of the present invention, projecting or casting a virtual tool of a known size onto the three-dimensional representation of the imaged tissue may include creating a virtual measurement tool having multiple extensions or lengths or arms in multiple directions and an origin point from which the extensions or lengths or arms extend, for example, as shown in FIGS. 3, 4A, 4B and/or 4C. The cursor according to embodiments of the present invention may be positioned on a certain area on the displayed image, for example, an area chosen by a professional or user as an area that requires inspection. In one example, a user may position the cursor or the graphic symbol of the virtual measurement tool on or near an area that appears abnormal in the displayed image, or an area suspected as ill or abnormal according to other parameters and/or examination.

Projecting or casting a virtual tool may further include positioning ending points of the tool's outline, border, contour, extensions or lengths on points defined by three coordinates in three-dimensional space, on the three-dimensional representation of the imaged tissue, wherein each of the ending points is positioned at an absolute distance $l$ from the point of interest in the three-dimensional representation. The positioning may be performed, for example, by evaluating or checking the absolute distance from the origin point to multiple points on the three-dimensional representation of the tissue along a certain direction. In case for a certain point the absolute distance equals the predetermined length $l$, the point may be set or determined as the position of an ending point.

Projecting of the virtual tool onto or adding it to the two-dimensional pixelated image may include creating a cursor such as, for example, cursors 310, 310a or 310b shown in FIG. 4A, 4B or 4C, respectively, that may have multiple projected dimensions or lengths in multiple directions, which are the distances on the two-dimensional image from the ending points, projected on the displayed image, to the point of interest, selected or marked on the displayed image, e.g., at the selected pixel or area representing the point of interest.

According to some embodiment of the invention, the projected virtual measurement tool, e.g., cursor, may be displayed upon a displayed image. The projected measurement tool may be moved over the displayed image, for example, by a user inputting movement commands, for example, by a mouse or keyboard or another suitable input device. In other embodiments, the virtual tool may be moved over the image automatically by the processor. The projected dimensions or lengths of the tool may be changed dynamically according to the distances on the two-dimensional image from the ending points, projected on the displayed image, to the point of interest, projected on the displayed image, wherein the point of interest is changed as the cursor moves over the displayed image.

It will be appreciated that the maximal size of the virtual tool, e.g., the absolute equal size of the tools' extensions or lengths, may be set by a user according to, for example, a typical and/or expected size of objects being examined or needs to be examined.

It may be appreciated that an image or frame may be a digital or analog representation of real-life objects and that reference to objects in the frame may refer to the visual representation of those objects. For example, the size of objects in an image may refer to a region of pixels in the image that visually represent a real-life object.

It is noted that while embodiments of the invention described herein are adapted for imaging of the GI tract, the devices and methods disclosed herein may be adapted for imaging other body cavities or spaces.

Different embodiments are disclosed herein. Features of certain embodiments may be combined with features of other embodiments; thus certain embodiments may be combinations of features of multiple embodiments.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method for size estimation of in-vivo objects, the method comprising using at least one hardware processor for:
   displaying a two-dimensional image of in-vivo objects obtained by an in-vivo imaging device;
   casting a virtual tool of a known size onto a three-dimensional space to determine ending points of the virtual tool, wherein coordinates in the three-dimensional space represent real world three-dimensional locations of in-vivo objects shown in the two-dimensional image relative to said in-vivo imaging device at the time of capturing said two-dimensional image; and
   projecting the ending points onto the two-dimensional image to generate an on-screen indication tool having a two-dimensional shape on the displayed image, the on-screen indication tool having multiple lengths in different directions, the lengths end at the determined ending points projected on the two-dimensional image.

2. The method of claim 1, further comprising using said at least one hardware processor for:
   receiving indication of a point of interest in the displayed two-dimensional image from a user; and
   calculating a three-dimensional coordinate representation of at least a plurality of image points around the point of interest,
   wherein the casting of the virtual tool onto the three-dimensional space comprises casting the virtual tool onto the three-dimensional coordinate representation.

3. The method of claim 2, further comprising using said at least one hardware processor for estimating the depth of the at least plurality of image points, wherein the three-dimensional coordinate representation is calculated based on the estimated depths.

4. The method of claim 1, further comprising using said at least one hardware processor for calculating a three-dimensional coordinate representation of the displayed two-dimensional image, wherein the casting of the virtual tool onto the three-dimensional space comprises casting the virtual tool onto the three-dimensional coordinate representation.

5. The method of claim 4, wherein the two-dimensional image comprises image pixels, further comprising using said at least one hardware processor for estimating the depth of each image pixel of the displayed two-dimensional image, wherein the three-dimensional coordinate representation is calculated based on the estimated depths.

6. The method of claim 1, further comprising using said at least one hardware processor for receiving from a user an indication of a point of interest in said displayed two-dimensional image, wherein the virtual tool comprises:
   an origin point; and
   a plurality of arms of a predetermined length, the arms extending from the origin point in multiple directions and end at the ending points,
   wherein the casting of the virtual tool onto the three-dimensional space comprises:
   calculating coordinates of the point of interest in the three-dimensional space; and
   calculating coordinates of a plurality of points located within a predetermined distance, equal to the predetermined length, from said point of interest in the three-dimensional space, wherein each of the plurality of points define an ending point of the ending points of the virtual tool;
   and wherein each of the multiple lengths of the on-screen indication tool extend from the point of interest to one of the projected ending points.

7. The method of claim 6, further comprising using said at least one hardware processor for moving the on-screen indication tool upon the displayed two-dimensional image and dynamically changing the lengths of the on-screen indication tool according to a received change of the point of interest.

8. The method of claim 6, wherein the predetermined length of the arms is five millimeters or 4.5 millimeters.

9. The method of claim 1, wherein the shape of the virtual tool is of an asterisk or of a closed curve.

10. The method of claim 1, wherein the size of the virtual tool is set according to the scope of sizes of in-vivo objects to be inspected.

11. A method for size estimation of in-vivo objects, the method comprising:
   displaying a two-dimensional image of in-vivo objects obtained by an in-vivo imaging device;
   calculating a three-dimensional coordinate representation of the displayed two-dimensional image;
   receiving from a user an indication of a point of interest in said displayed two-dimensional image;
   casting the point of interest onto the three-dimensional representation;
   calculating coordinates of a plurality of points located within a predetermined distance from the point of interest in the three-dimensional representation, wherein each of the plurality of points define an ending point of a virtual tool having an origin point at the point of interest; and projecting the plurality of ending points onto the two-dimensional image to generate an on-screen indication tool having a two-dimensional shape on the displayed image, the on-screen indication tool having multiple lengths in different directions, each length extending from said point of interest to one of the projected ending points.

12. A system for size estimation of in-vivo objects, the system comprising:
a monitor;
a processor configured to:
display a two-dimensional image of in-vivo objects on the monitor, wherein the two-dimensional image is obtained by an in-vivo imaging device;
cast a virtual tool of a known size onto a three-dimensional space to determine ending points of the virtual tool, wherein coordinates in the three-dimensional space represent real world three-dimensional locations of in-vivo objects shown in the two-dimensional image relative to said in-vivo imaging device at the time of capturing said two-dimensional image; and
project the ending points onto the two-dimensional image to generate an on-screen indication tool having a two-dimensional shape on the displayed image, the on-screen indication tool having multiple lengths in different directions, the lengths end at the determined ending points projected on the two-dimensional image.

13. The system of claim 12, further comprising a user input device, wherein the processor is further configured to:
receive indication of a point of interest in the displayed two-dimensional image from a user via the user input device; and
calculate a three-dimensional coordinate representation of at least a plurality of image points around the point of interest,
wherein the casting of the virtual tool onto the three-dimensional space comprises casting the virtual tool onto the three-dimensional coordinate representation.

14. The system of claim 13, wherein the processor is further configured to estimate the depth of the at least plurality of image points, wherein the three-dimensional coordinate representation is calculated based on the estimated depths.

15. The system of claim 12, wherein the processor is further configured to calculate a three-dimensional coordinate representation of the displayed two-dimensional image, and wherein the casting of the virtual tool onto the three-dimensional space comprises casting the virtual tool onto the three-dimensional coordinate representation.

16. The system of claim 15, wherein the two-dimensional image comprises image pixels, wherein the processor is further configured to estimate the depth of each image pixel of the displayed two-dimensional image, and wherein the three-dimensional coordinate representation is calculated based on the estimated depths.

17. The system of claim 12, further comprising a user input device, wherein:
the processor is further configured to receive from a user an indication of a point of interest in said displayed two-dimensional image via the user input device,
the virtual tool comprises:
an origin point; and
a plurality of arms of a predetermined length, the arms extending from the origin point in multiple directions and end at the ending points,
the casting of the virtual tool onto the three-dimensional space comprises:
calculating coordinates of the point of interest in the three-dimensional space; and
calculating coordinates of a plurality of points located within a predetermined distance, equal to the predetermined length, from said point of interest in the three-dimensional space, wherein each of the plurality of points define an ending point of the ending points of the virtual tool;
and wherein each of the multiple lengths of the on-screen indication tool extend from the point of interest to one of the projected ending points.

18. The system of claim 17, wherein the processor is further configured to move the on-screen indication tool upon the displayed two-dimensional image and dynamically change the lengths of the on-screen indication tool according to a received change of the point of interest.

19. The system of claim 17, wherein the predetermined length of the arms is five millimeters or 4.5 millimeters.

20. The system of claim 12, wherein the shape of the virtual tool is of an asterisk or of a closed curve.

* * * * *